United States Patent [19]

Hth et al.

[11] Patent Number: 5,252,321

[45] Date of Patent: Oct. 12, 1993

[54] BIOCIDAL POLYMERS AND POLYMER DISPERSIONS, PROCESSES FOR THEIR PREPARATION AND THEIR USE

[75] Inventors: Hans-Ullrich Hth, Egelsbach; Wolfgang Lindner, Seelze, both of Fed. Rep. of Germany

[73] Assignee: Hoechst Aktiengesellschaft, Fed. Rep. of Germany

[21] Appl. No.: 994,138

[22] Filed: Dec. 21, 1992

[30] Foreign Application Priority Data

Dec. 21, 1991 [DE] Fed. Rep. of Germany ....... 4142731

[51] Int. Cl.$^5$ ................................................ A61K 9/10
[52] U.S. Cl. ............................. 424/78.32; 424/78.22; 424/78.09; 526/259; 526/278; 526/287; 524/547; 524/548; 524/809
[58] Field of Search ............... 424/78.09, 78.22, 78.32; 526/259; 524/547, 548, 809

[56] References Cited

U.S. PATENT DOCUMENTS 2,623,879 12/1952 Ringwald et al. .............. 526/259 X

FOREIGN PATENT DOCUMENTS 2583753 12/1986 France .
3252462 11/1991 Japan .

OTHER PUBLICATIONS

Copy of 1990 Carbendazim pp. 123–124.
Copy of Agrochemicals vol. 108, 1988 pp. 235–236.

*Primary Examiner*—Joseph L. Schofer
*Assistant Examiner*—Mark Nagumo
*Attorney, Agent, or Firm*—Bierman and Muserlian

[57] ABSTRACT

Preparation of biocidal polymers and copolymers based on free radical-polymerizable and copolymerizable ethylenically unsaturated monomers containing monomer units composed of BCM salts of ethylenically unsaturated carboxylic acids, sulfonic acids or phosphonic acids, solutions thereof and preferably aqueous dispersions thereof. Processes for their preparation and their use as fungicidal and algicidal impregnating agents, paints and finishing agents for scumbles and dispersion paints providing protection against blue staining on wood, for synthetic resin renderings, for exposed concrete paints and for textile finishing agents.

5 Claims, No Drawings

BIOCIDAL POLYMERS AND POLYMER DISPERSIONS, PROCESSES FOR THEIR PREPARATION AND THEIR USE

The invention relates to biocidal polymers and copolymers, preferably aqueous biocidal plastic dispersions, processes for their preparation by free radical polymerization or copolymerization from monomeric BCM salts of ethylenically unsaturated and free radical-polymerizable or copolymerizable acids and their use as fungicidal and algicidal paints and finishing agents, as scumble for wood protection, for dispersion paints with protection against blueing on wood, for synthetic resin renderings, for paints for exposed concrete and for textile finishing agents.

Many types of wood, including numerous home-grown woods, have only a low natural durability. Especially when exposed to the effects of moisture, for example when used outside closed rooms or within damp and poorly ventilated rooms, the risk of the colonization and destruction of wood left in the natural state by fungi and microorganisms is high. There has therefore been no lack of attempts to reduce the susceptibility of timber. Thus, solutions or mixtures of polymer binders with fungicidal compounds, frequently phenol derivatives, such as, for example, PCP, trichlorophenols, ortho-phenylphenol (for example Preventol), polyhalogenated hydrocarbons (for example the insecticide HCH or the fungicide 2,4,5,6-tetrachloro-m-phthalodinitrile (Nopcocide N40)) or tin compounds (tributyltin oxide) or their reaction products with carboxylic acids, such as, for example, oleic acid, naphthenic acid or benzoic acid, in combination with organic solvents have been and are still frequently being used as wood protection agents. Disadvantages of these systems are, inter alia, considerable toxicological reservations with regard to the active compounds, the combustibility of many of these agents and their powerful inherent odor, which precludes or restricts use in, for example, living areas, and also the high price of the solvents and the negative effects on human health and the environment when they are released into the air. In addition, the efficiency of the wood protection agents disclosed hitherto often also declines rapidly, since the biocidal active compounds, despite the fact that they are frequently insoluble in water, are relatively rapidly leached out, for example on exposure to weather, or are displaced via the gas phase and are then able to contaminate the environment as a consequence of their usually inadequate biodegradability.

The use of anionic plastic dispersions as binders for paints and renderings and for scumble treatment of wood has already been disclosed. Products of this type are environmentally friendly and comply very well with the requirements for a wood coating, including from the aesthetic standpoint. A disadvantage is that when they are used on their own they are not able, because of the lack of biocidal activity, to protect the wood adequately against decay and infestation by fungi. An effective addition of the abovementioned free active compounds, such as phenol compounds, polyhalogenated hydrocarbons, tin compounds, with their associated disadvantages which have already been mentioned is, however, possible only with difficulty. They can, for example, not be recommended for interior use, in particular on toxicological grounds. Moreover, despite their insolubility in water, when used outdoors they also provide only short-term protection when subjected to leaching out.

There has therefore been no lack of attempts to replace the active compounds used hitherto by new suitable active compounds less toxic to mammals. However, the active compounds disclosed hitherto usually have the disadvantage that they act only against a specific fungus and, in some cases, have to be added to the plastic dispersions in the form of organic solutions, with correspondingly undesirable consequences, or in the form of solids, which demands additional measures for mixing in and in the case of polar active compounds frequently resulted in excessive leaching out from paints prepared therefrom.

Especially when providing aqueous or water-dilutable binders, such as plastic dispersions or water-soluble resins, such as are nowadays increasingly used in all coating sectors, with a biocidal finish, there are further problems. Thus, some of the new active compounds are not stable in an aqueous environment and are hydrolyzed, with loss of activity, when the binder is stored (example: PREVENTOL A 4=N,N-dimethyl-N'-phenyl-N'-(fluorodichloromethylthio)sulfamide or PREVENTOL A 5=N,N-dimethyl-N'-phenyl-N'-(fluorodichloromethylthio)-sulfamide).

Some of the other, usually organic, compounds are sparingly soluble in water and therefore can be introduced only with difficulty or via polar auxiliary solvents or solubility promoters.

Whereas there are new environmentally friendly application methods and also new active compounds (for example Xyligen B (triazole derivative)) for the protection of wood against wood-destroying fungi (for example from the group comprising the Basidiomycetes, such as, for example, *Poria monticola, Gleophyllum trabeum, Lenzites trabea, Lentinus lepideus, Coniophora puteana, Trametes versicolor*) by dipping in solutions containing active compound, the infestation with blue stain fungi in the outside regions of fences and wooden window frames is still a problem which cannot be solved satisfactorily.

It is known that BCM (benzimidazolylcarbamic acid methyl ester) is a compound which has a very good fungicidal action both against blue stain fungi (for example *Aureobasidium pullulans* and *Sclerophoma pityophila*) and against molds (such as *Aspergillus niger*) and soft rot fungi (for example *Chaetomium globosum*), i.e. that it advantageously has a very broad spectrum of action.

A disadvantage is the exceptionally low solubility in all conventional organic solvents and also, in particular, in water. The reaction with reactive organic compounds to give derivatives which have better solubility or covalent linking to the binder via functional groups during the polycondensation reaction is indeed possible, but hitherto this has led to a reduction in the biocidal action extending to complete loss of protection. Hitherto the only possibility for fungicidal treatment of a binder with BCM consisted in adding BCM as active compound in powder form to the binder formulation and incorporating well. Transparent thick or thin film scumbles are, however, not obtainable by this means since the active compound in the requisite concentration causes the coating to appear opaque, which is undesirable in the case of exterior use on window frames and fences. Particularly in the field of aqueous binders, such as watersoluble resins or plastic dispersions, where a very good biocidal spectrum of properties can be complemented by up-to-date protection of the environment and the workforce, it would be necessary to be able to employ an ideal and universal biocidal active compound which remains biocidally active without time limit in the binder formulations and the paints, coatings and impregnations prepared therefrom.

The object on which the invention was based was, thus, to provide an environmentally friendly, biocidal binder, preferably in the form of an aqueous plastic dispersion, which is suitable for the preparation of coating compositions or primers providing wood with protection against blueing, in which the biocidal active compound is distributed as homogeneously as possible and has as long as possible a period of biocidal action coupled with a broad spectrum of action, and the biocidal active compound has low leachability and optionally also protects against infestation by algae, which can often be important, for example for facades and for exposed concrete.

It has now been found, surprisingly, that the abovementioned difficulties can be overcome and the stated object can be achieved if dispersions of polymers are used in which the macromolecules contain monomer units composed of benzimidazolylcarbamic acid methyl ester salts (BCM salts) of ethylenically unsaturated carboxylic acids or ethylenically unsaturated sulfonic acids or ethylenically unsaturated phosphonic acids, preferably of ethylenically unsaturated carboxylic acids.

The invention therefore relates to biocidal polymers or copolymers based on free radical-polymerized or copolymerized ethylenically unsaturated monomers, wherein the polymers or copolymers contain monomer units composed of BCM salts of the formula I

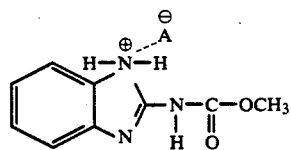

(I)

in which $A^{\ominus}$ is an anionic ethylenically unsaturated carboxylic acid or sulfonic acid or phosphonic acid radical, and said monomer units are polymerized in the biocidal macromolecules via the ethylenic double bond of the radical $A^{\ominus}$, or solutions or aqueous dispersions of said polymers or copolymers, preferably aqueous dispersions.

The content of monomer units composed of BCM salts of the formula I in the biocidal polymers or copolymers is variable over a wide range and is preferably 0.001 to 5% by weight, in particular 0.02 to 1% by weight, with respect to the biocidal polymer or copolymer. The biocidal macromolecules can also contain monomer units composed of different BCM salts of the formula I, preferably those having acid radicals of the same type in the radical $A^{\ominus}$. Homopolymers or copolymers of BCM salts of the formula I are also possible and can be advantageous in some cases.

According to the invention, the biocidal polymers or copolymers preferably contain such monomer units composed of BCM salts of the formula I in which the anionic radical $A^{\ominus}$ in formula I is an acrylate, methacrylate, fumarate, maleate, crotonate, itaconate, styrenesulfonate, acrylamidomethylpropanesulfonate, acrylamidoglycolic acid methyl ether, vinylsulfonate, vinylphosphonate or acrylamidomethylphosphonate radical. Particularly preferred anionic radicals $A^{\ominus}$ are acrylate, methacrylate, vinylsulfonate and acrylamidomethylpropanesulfonate radicals.

The invention also relates to the biocidal monomeric BCM salts of the formula I, in which the radical $A^{\ominus}$ in formula I has the abovementioned meanings.

According to the invention, the biocidal monomeric BCM salts of the formula I can be obtained by reaction of stoichiometric amounts of BCM and monomeric ethylenically unsaturated acids of the formula HA, in which A has the same meaning as $A^{\ominus}$ in formula I. The reaction can be carried out in bulk. However, it is preferably carried out in aqueous solution, the acid of the formula HA being dissolved in water and the BCM being introduced into the aqueous solution, the reaction taking place with a slight rise in the temperature of the solution. By cooling the aqueous solution to close to the freezing point of water, the resulting BCM salt of the formula I crystallizes out and can be obtained in pure form.

The BCM salts of the formula I prepared according to the invention are generally readily soluble, both in water and in customary free radical-polymerizable and/or copolymerizable ethylenically unsaturated monomers. The BCM salts of the formula I can therefore be used directly and without problems for emulsion and suspension polymerization or copolymerization in an aqueous medium or also for solution or bulk polymerization or copolymerization in organic solvents, or in the form of a solution in corresponding comonomer components. The polymerization and copolymerization of the BCM salts of the formula I is preferably to be carried out in the absence of excess free inorganic or free non-copolymerizable organic acids since otherwise, in particular in aqueous media, there is a risk of anion exchange between the BCM salts of the formula I and the free acids, which can lead to disadvantages.

Biocidal polymers or copolymers according to the invention containing contents according to the invention of monomer units composed of BCM salts of the formula I, their solutions or their aqueous dispersions can also be obtained by reacting corresponding starting polymers or copolymers which contain monomer units of the formula HA, in which A has the meaning as in formula I, in their acid HA form, in anhydrous polar organic solvents with a stoichiometric amount of pulverulent BCM or soluble BCM salt of a low-molecular weak acid, preferably a weak organic acid which can be distilled in its free form, removing the weak organic acid which may have been liberated, preferably by distillation, and isolating the biocidal polymer or copolymer according to the invention from the organic solution in the conventional manner, or, after adding emulsifier, converting it into an aqueous dispersion and then optionally removing the polar solvent, preferably by distillation. Suitable polar organic solvents are, for example, inert, low-molecular alcohols, esters, ethers and ketones, preferably methanol, propanol, ethyl acetate, acetone, methyl ethyl ketone, dioxane and tetrahydrofuran.

A few characteristic properties of monomeric BCM salts of the formula I, such as, for example, the melting point, the solubility in water and the solubility in butyl acrylate, are summarized in Table 1.

TABLE 1

Properties of monomeric, polymerizable BCM salts of the formula I

| BCM salt of the formula I | Melting point °C. (capillary method) | Solubility in $H_2O$ at 25° C. | Solubility in butyl acrylate at 25° C. |
|---|---|---|---|
| $[BCM]H^\oplus$ $CH_2=CHCOO^\ominus$ | 195 (with decomp.) | <10% | <10% |
| $[BCM]H^\oplus$ $CH_2=C-COO^\ominus$ <br>                $\|$ <br>                $CH_3$ | 235 (with decomp.) | <5% | <10% |
| $[BCM]H^\oplus$—C$_6$H$_4$(—CH=CH$_2$)(—SO$_3^\ominus$) | polymerizes on recrystallization | >20% | <10% |
| $[BCM]H^\oplus$ $CH_2=CH-CONH-C(CH_3)_2-CH_2-SO_3^\ominus$ | 90-91 | >20% | <10% |
| $[BCM]H^\oplus$ $CH_2=CH-P(CH_3)(=O)(O^\ominus)$ | — | >20% | <10% |

For polymerization the BCM salts of the formula I can be used either in bulk or in the form of solutions of the BCM salt in the aqueous acid HA or in the free acid HA. When preparing finely divided aqueous pure acrylate or styrene-acrylate dispersions, in which the starting comonomers used in many cases contain ethylenically unsaturated acids such as acrylic acid (AA) or methacrylic acid (MAA), the amount of BCM stoichiometrically required for salt formation is advantageously dissolved in the requisite amount of the ethylenically unsaturated acid with formation of the salt and the solution of the resulting monomeric BCM salt in the unsaturated acid is used in place of the pure unsaturated acid. If BCM salts of the formula I are used in the preparation of cationic (Example 5) or amphoteric dispersions (Example 4), dispersions result which have very good fungicidal activity and, at the same time, particularly high algicidal activity. The level of activity against one or other microorganism can also be varied within wide limits by means of the choice of the nature and amount of the cationic surfactant to be used.

The invention therefore also relates to the use of aqueous biocidal plastic dispersions according to the invention which are based on free radical-polymerized or copolymerized ethylenically unsaturated monomers having biocidally active contents of monomer units of the formula I for the impregnation and priming of absorbent substrates and for painting or coating solid substrates, the biocidal plastic dispersions being anionic or cationic or amphoteric dispersions which contain biocidally active dispersion polymers or copolymers, in which the polymer particles have average particle diameters of 0.02 to 1 μm, preferably 0.05 to 0.5 μm.

According to the invention, the dispersions are preferably used for impregnating and priming absorbent substrates, in particular rendered surfaces in the building sector, including sanded-down plaster, and wood, paper and cellulose-containing products, and also for painting or coating any desired solid substrates and also as textile finishing agents.

The solids content of the biocidal dispersions to be used according to the invention is not critical. Preferably, however, it is 5 to 70% by weight, in particular 10 to 60% by weight, with respect to the dispersion.

A further preferred embodiment of the invention is that wherein the dispersions contain dispersion copolymers in which the macromolecules contain monomer units, calculated in % by weight, with respect to the copolymer, from the following monomer groups:

a) 80 to 99.9% by weight, preferably 90 to 99% by weight, of ethylenically unsaturated hydrophobic monomers, preferably from the group comprising vinyl esters, methacrylic esters, acrylic esters and vinyl-aromatic compounds, b) 0.001 to 5% by weight, preferably 0.02 to 1% by weight of BCM salts of the formula I, in which $A^\ominus$ has the abovementioned meaning, c) 0 to 10% by weight, preferably 0.5 to 5% by weight, of ethylenically unsaturated cationic water-soluble monomers, which contain, as cationic groups, quaternized alkylammonium, alkylsulfonium or alkylphosphonium groups, preferably alkylammonium groups, the alkyl radicals of which in each case have 1 to 24 carbon atoms, it being possible for individual alkyl radicals or several alkyl radicals, preferably individual alkyl radicals, to be replaced by ($C_5$-C)-cycloalkyl, ($C_7$-$C_{12}$)-aralkyl or ($C_1$-$C_{18}$)-alkyl radicals, preferably benzyl, methyl, ethyl or —$CH_2CONH_2$, and d) 0 to 19% by weight, preferably 0.1 to 6% by weight, of ethylenically unsaturated hydrophilic monomers containing one or more functional groups from the series comprising —OH, —COOH, —$SO_3H$, —PO(OH) and —$CONR^1R^2$, in which $R^1$ and $R^2$, which can be identical or different, are H or —$CH_2OR$, where R=H or ($C_1$-$C_8$)-alkyl, and the dispersions also contain 0.1 to 20% by weight, preferably 0.1 to 7% by weight, of surface-active compounds from the group comprising anionic, nonionic, cationic or amphoteric emulsifiers and also, optionally, in addition between 0 and 5% by weight, preferably 0.1 to 2% by weight, of protective colloids, in each case with respect to the total amount of monomer.

The preparation of aqueous anionic, cationic or amphoteric plastic dispersions according to the invention can be effected by conventional emulsion polymerization or copolymerization, for example by the feed or preemulsion process at 20° to 100° C., preferably at 50° to 90° C. In this process, in the conventional manner, a portion of the monomers is preferably prepolymerized in the aqueous liquor and the residual amount metered in continuously, maintaining the polymerization reaction. In order to obtain a particularly high content of BCM cations on the surface of the dispersion polymer or copolymer particles it is possible, preferably in the case of copolymerizations, to meter in, for example, the monomeric BCM salts of the formula I in non-uniform amounts during the course of the polymerization, particularly advantageously in relatively large amounts together with other comonomers at the start of the polymerization. The solids content of the biocidal plastic dispersions obtainable in the case of emulsion polymerization is in the range customary for the preparation of known anionic or nonionic paint binder dispersions.

When plastic dispersions to be used according to the invention are prepared by emulsion copolymerization, the monomer components as can be assigned to the group listed above under a), which are used are preferably copolymerizable, ethylenically unsaturated hydrophobic compounds, such as vinyl esters of $(C_1-C_{18})$-carboxylic acids, preferably, for example, vinyl acetate, vinyl propionate, vinyl versatate, vinyl laurate or vinyl stearate; (meth)acrylic esters of $(C_1-C_8)$-alcohols, preferably, for example, methyl methacrylate, butyl methacrylate, octyl methacrylate, ethyl acrylate, isobutyl acrylate and 2-ethylhexyl acrylate; vinyl-aromatic compounds, preferably, for example, styrene or vinyltoluene; vinyl chloride, ethylene, acrylonitrile, diesters of maleic acid and/or fumaric acid or vinylpyrrolidone. The monomers can be used either on their own or as a mixture. Preferably, those monomers are used which lead to stable dispersion polymers and copolymers resistant to saponification. The choice of monomers and their mixing ratios usually depends on the desired application properties of the dispersion, it being possible to apply the customary selection criteria known to those skilled in the art for their formulations.

In particular, the minimum film-forming temperature (MFT) of the plastic dispersions should be below the range, or at most within the range, of the intended use temperatures, i.e. preferably between 0° and 80° C. and in particular between 0° and 40° C. If polymers of harder formulation are used, film-forming auxiliaries or external plasticizers can be used in order to achieve the requisite MFT, in which case the effect thereof on the biocidal properties of the dispersions should be checked beforehand. If such additives are not desired, the MFT of the cationic dispersions should preferably be in the range from 0° to 25° C. The following comonomer combinations are suitable in combination with monomeric BCM salts of the formula I and cationic monomers, very particularly, for example, in the weight ratios indicated below (pwt=parts by weight), for the preparation of aqueous biocidal cationic dispersions according to the invention:

| | |
|---|---|
| Butyl acrylate/methyl methacrylate | 10–90 pwt/90–10 pwt |
| Butyl acrylate/styrene | 10–90 pwt/90–10 pwt |
| Octyl acrylate/methyl methacrylate | 5–80 pwt/95–20 pwt |
| Octyl acrylate/styrene | 5–80 pwt/95–20 pwt |
| Vinyl acetate/butyl acrylate | 40–80 pwt/60–20 pwt |
| Vinyl acetate/vinyl versatate | 50–80 pwt/50–20 pwt |

However, the contents of monomer units of BCM salts of the formula I are decisive for the biocidal properties, according to the invention, of the dispersions.

In the case where an improvement and optimization of the algicidal properties of the biocidal dispersions are desired at the same time, it is no less important to use water-soluble cationic ethylenically unsaturated and copolymerizable monomers containing quaternary alkylsulfonium, alkylphosphonium or, in particular, alkylammonium groups, it being possible for the alkyl radicals in each case to have 1–24 carbon atoms or also to be combined to form a ring structure, but in particular can be a $(C_5-C_7)$-cycloalkyl, $(C_7-C_{12})$-aralkyl or $(C_1-C_{18})$-alkyl radical, methyl, ethyl, benzyl or $H_2N-CO-CH_2$ radicals being preferred. The concentration of these monomers should be 0.1 to 10% by weight, preferably 0.5 to 5% by weight, with respect to the total amount of all monomers.

Preferred quaternized cationic monomers are, for example,
trimethylammonioethyl acrylate chloride,
trimethylammonioethyl methacrylate chloride,
β-acetamido-diethylaminoethyl acrylate chloride,
β-acetamido-diethylaminoethyl methacrylate chloride,
acrylamidopropyltrimethylammonium chloride,
methacrylamidopropyltrimethylammonium chloride,
acrylamidoethyltrimethylammonium chloride,
methacrylamidoethyltrimethylammonium chloride,
trimethylammonioneopentyl acrylate chloride,
trimethylammonioneopentyl methacrylate chloride,
diallyl-dimethylammonium chloride and
diallyl-butylmethyl-ammonium chloride.

With respect to the spectrum of properties of the polymer dispersions to be used according to the invention it can be advantageous in some cases to use yet further comonomers in the emulsion copolymerization, specifically ethylenically unsaturated compounds containing functional groups such as —OH, —COOH, —SO$_3$H, —PO(OH), —NR$^1$R$^2$ or —CONR$^1$R$^2$, where R$^1$ and R$^2$ can be identical or different and are H or —CH$_2$OR, where R=H or $(C_1-C_8)$-alkyl.

Preferred compounds from this group are, for example, hydroxyethyl methacrylate, hydroxypropyl methacrylate, polyhydroxypropyl methacrylate, hydroxyethyl acrylate, hydroxypropyl acrylate, polyhydroxypropyl acrylate, methacrylic acid, acrylic acid, crotonic acid, maleic acid, fumaric acid, itaconic acid and also the half-esters of the latter three compounds, acrylamidomethanesulfonic acid, dimethylaminoneopentyl methacrylate, dimethylaminopropylmethacrylamide, dimethylaminoethyl methacrylate, dimethylaminoethyl acrylate, 2-N-morpholinoethyl methacrylate, t-butylaminoethyl methacrylate, methacrylamide, acrylamide, N-methylolmethacrylamide, N-methylolacrylamide, vinylsulfonic acid and salts thereof, acrylamidomethylpropanesulfonic acid and vinylphosphonic acid.

When using ethylenically unsaturated copolymerizable carboxylic acids, the proportion thereof should preferably be less than 10% by weight, in particular between 0.1 and 6% by weight, with respect to the total amount of all monomers.

To adjust the particle size of the dispersions to the desired fineness (average particle diameter 0.02 to 1.0

μm, preferably 0.05 to 0.5 μm, in particular 0.08 to 0.15 μm), anionic or cationic and/or nonionic and/or amphoteric surface-active emulsifiers are used in the emulsion polymerization in the customary manner, in an amount of 0.1 to 20% by weight, preferably 0.12 to 7% by weight and in particular 1 to 5% by weight, with respect to the total amount of monomers. It has been found that the optimum amounts of these emulsifiers required according to the invention in the dispersions surprisingly do not adversely affect the waterproof properties of basecoats and impregnations.

The emulsifiers used are preferably conventional nonionic surfactants, for example from the group comprising the reaction products of epoxides, such as, for example, ethylene oxide, with aliphatic, cycloaliphatic, araliphatic, aliphatic-aromatic or aromatic carboxylic acids, alcohols, phenols or amines, and also block copolymers composed of different epoxides, such as, for example, ethylene oxide and propylene oxide.

In addition, conventional anionic surfactants, preferably, for example, surface-active ammonium salts and alkali metal salts of fatty acids (soaps), fatty alcohol sulfates, isethionic acid ethers of fatty alcohols, alkanesulfonates, alkyl benzenesulfonates, (oxethylated) sulfosuccinic acid esters, polyoxethylated fatty alcohol sulfates, alkylphenol polyoxethylate sulfates or (alkyl)-naphthol polyoxethylate sulfates and fatty alcohol phosphates can be used.

Further preferred emulsifiers are, for example, primary, secondary and tertiary fatty amines in combination with organic or inorganic acids and also, in addition, surface-active quaternary alkylammonium compounds. In addition, in some cases, amphoteric surfactants of zwitterionic structure, for example of the betaine type, can also be advantageous. The said emulsifiers can be used either on their own or in combination with the same type or a different type in the conventional manner, provided they do not adversely affect one another because of opposite charges or impair the stability of the dispersion.

Known protective colloids, specifically preferably those based on high molecular weight organic compounds, which are water-soluble or water-dispersible, develop essentially no or no pronounced interfacial activity and have a pronounced dispersing power can also be co-used in the preparation of the cationic dispersions. Preferred protective colloids are, for example, cellulose ethers, polyvinyl alcohols, polysaccharides and polyvinylpyrrolidones, it being possible for these to contain acid/anionic or basic or cationically functional groups. The selection depends on the particular type of dispersion and must not lead to disturbance of the coulomb repulsion of the latex particles, i.e. protective colloids having opposite charges can in general not be used at the same time.

The amounts of protective colloid to be used depend on the desired dispersion properties, in particular the fineness of the dispersion particles. Preferably protective colloid amounts of between 0 and 5% by weight, in particular between 0.1 and 2% by weight, with respect to the total amount of monomers, are optionally used in the emulsion polymerization.

All of the preferably water-soluble and radical chain-initiating systems customary in emulsion polymerization can be used to initiate the polymerization or copolymerization. Preferred initiators in the case of the anionic types are, for example, persulfates, such as ammonium persulfate, sodium persulfate and potassium persulfate; in the case of the purely cationically charged dispersion types, on the other hand, the compounds used are, rather, those such as 2,2'-azobis(2-amidinopropane) dihydrochloride, 2,2'-azobis-(N,N'-dimethyleneisobutyramidine) dihy-drochloride, 4,4'-azobis-(4-cyanovaleric acid), $H_2O_2$ or t-butyl hydroperoxide The following, for example, are also generally usable: redox systems, such as $H_2O_2$ and ascorbic acid, peroxides and polyvalent metal salts, t-butyl hydroperoxide and Rongalite, it being possible for redox systems to be advantageous, in particular, for lowering the residual monomer content in the post-reaction stage of the polymerization, and also energy-rich radiation as well as conventional photoinitiators.

In order to control the molecular weight during the emulsion polymerization it is also possible to use conventional regulators, such as, for example, mercaptans or halogenated hydrocarbons in order to lower the molecular weight or, alternatively, optionally up to 5% by weight, with respect to the total amount of monomers, of polyethylenically unsaturated or multifunctional compounds capable of crosslinking, such as, for example, divinylbenzene, ethylene glycol dimethacrylate, ethylene glycol diacrylate, butanediol dimethacrylate, butanediol diacrylate, triallyl cyanurate, melamine or isocyanatoethyl methacrylate, in order to increase the molecular weight.

For the use, according to the invention, of aqueous or finely divided plastic dispersions as priming and impregnating agents, the solids content thereof can preferably be adjusted to values of 3 to 40% by weight, in particular 5 to 20% by weight. In these preferred solids concentration ranges, the dispersions have a low viscosity and a high penetrating power into absorbent substrates; in addition, the cationic dispersions according to the invention surprisingly also have the advantage of generating virtually no troublesome foam and can therefore be processed particularly advantageously.

The invention is illustrated in more detail by the following examples.

EXAMPLE 1

206 9 g of desalinated water (D water) and 1.9 g of sodium lauryl polyglycol ether sulfate (emulsifier) are initially introduced into a 2 1 three-necked round-bottomed flask provided with a stirrer, a dropping funnel and a reflux condenser. An emulsion is prepared from 182.1 g of methyl methacrylate, 183.1 g of butyl acrylate, 11.25 g of acrylic acid, which additionally contain 1.1 g of benzimidazolylcarbamic acid methyl ester (BCM) in solution, with salt formation, 0.95 g of ammonium persulfate (APS), 3.75 g of sodium lauryl polyglycol ether sulfate and 243.75 g of D water, and 15 g of this emulsion are added to the aqueous emulsifier solution initially introduced. The vessel is heated, with stirring, to 80° C., 0.175 g of APS already being added at 55° to 60° C. in order to start the polymerization. The residual monomer emulsion is metered into the vessel in the course of 3.5 hours, with stirring, at 80° C. After a post-reaction stage of 2.5 hours, the reaction mixture is cooled to room temperature (RT). 15 ml of 17% strength by weight ammonia are added to the reaction mixture one hour after all of the monomer emulsion has been metered in and after cooling to RT has taken place. A further 17% by weight ammonia is added in an amount such that the resulting dispersion has a pH value of 8.5.

An anionic dispersion is obtained which has a solids content (S content) of 44.7% by weight, with respect to the dispersion, and a minimum film-forming temperature (MFT) of 7° C. The BCM content of the copolymer is 0.28% by weight, with respect to the copolymer.

EXAMPLE 2

420 g of D water and also 11.8 g of sodium lauryl sulfate and 4.8 g of oxethylated nonylphenol (emulsifier combination) are initially introduced into a stirred reactor as described in Example 1.

An emulsion is prepared from 663.1 g of D water, 25.5 g of sodium lauryl sulfate, 6.8 g of oxethylated nonylphenol, 236.7 g of styrene, 289.3 g of butyl acrylate, 7.1 g of acrylic acid, 13.1 g of methacrylic acid and 1.45 g of BCM methacrylate, which had been prepared separately beforehand, and 110 g of this emulsion are added to the aqueous emulsifier solution initially introduced. The vessel is heated to 80° C. with stirring, 10 ml of an initiator solution composed of 2 g of ammonium persulfate and 40 g of D water being added thereto at 60° C. After prepolymerization for 15 minutes, the residual monomer emulsion is metered in in the course of 3 hours and the residual initiator solution is metered in in parallel. After heating at 80° C. for a further 2 hours, the reaction mixture is cooled to RT.

A finely divided, coagulate-free anionic dispersion is obtained which has an S content of 34.1% by weight, a pH value of 3.4 and a MFT of 12° C. The BCM content of the copolymer is 0.24% by weight, with respect to the copolymer.

EXAMPLE 3

Example 1 is repeated except that a mixture of 258.9 g of butyl acrylate, 93.7 g of methyl methacrylate and 93.7 g of styrene is used in place of 182.1 g of methyl methacrylate and 183.1 g of butyl acrylate, and the 11.25 g of acrylic acid and the 1.1 g of BCM are replaced by a mixture of 5.3 g of BCM-AMPS salt (BCM acrylamidomethylpropanesulfonate), 2.5 g of acrylic acid and 5.1 g of methacrylic acid. After the end of the polymerization and cooling the reaction mixture to RT, a fine to medium disperse, coagulate-free anionic dispersion is obtained which has a solids content of 49.8% by weight, a pH value of 4.1 and a MFT of 11° C. The BCM content of the copolymer is 0.56% by weight, with respect to the copolymer.

EXAMPLE 4

1117.5 g of D water, 4.5 g of oxethylated tridecyl alcohol, 4.5 g of dimethyldidecylammonium chloride, 9 g of stearyldimethylbenzylammonium chloride and 18 g of a 50% strength by weight aqueous methacrylamidopropyltrimethylammonium chloride solution are initially introduced into a stirred reactor as described in Example 1. After adding 45 g of a monomer mixture composed of 229.5 g of butyl acrylate, 220.5 g of methyl methacrylate, 3.25 g of BCM methacrylate, 1.5 g of methacrylic acid, 2.23 g of BCM acrylate and 0.76 g of acrylic acid, the vessel is heated to 80° C., 0.9 g of 4,4'-azobiscyanovaleric acid (AVA) are added and the mixture is prepolymerized for 15 minutes. A further 0.9 g of AVA is then added and the residual monomer mixture is added dropwise in the course of 2 hours at 80° C., with stirring. After a further addition of 0.45 g of AVA, the mixture is heated for a further one hour at 80° C. and cooled to RT. The resulting finely divided amphoteric dispersion has an S content of 30.3% by weight, a pH value of 2.6 and a MFT of 6° C. and is coagulate-free. The BCM content of the copolymer is 0.21% by weight, with respect to the copolymer.

EXAMPLE 5

1186.2 g of D water, 19.5 g of 50% strength by weight aqueous methacrylamidopropyltrimethylammonium chloride solution, 19.5 g of laurylpyridinium chloride and 48 g of a monomer mixture composed of 258.4 g of butyl acrylate, 229.1 g of methyl methacrylate, 9.8 g of hydroxyethyl methacrylate and 7.3 g of BCM-AMPS salt (see Example 3) are initially introduced into a stirred reactor as described in Example 1 and heated to 80° C. After adding 1.95 g of AVA and prepolymerizing for 15 minutes, the residual monomer mixture is metered in in the course of 2 hours. A further 0.48 g of AVA, which has been dissolved in 10 g of D water at pH 7 with co-use of aqueous NaOH, is then added and the reaction mixture is stirred for 30 minutes at 80° C. After cooling to RT, a finely divided cationic dispersion is obtained which is free from coagulate and has an S content of 30% by weight, a pH value of 3.5 and a MFT of <0° C. The BCM content of the copolymer is 0.65% by weight, with respect to the copolymer.

COMPARISON EXAMPLE 1

Example 1 is repeated except that the 1.1 g of BCM are omitted. A finely divided anionic dispersion is obtained which has a solids content of 44.8% by weight and a MFT of 7° C.

COMPARISON EXAMPLE 2

Example 2 is repeated except that the 1.45 g of BCM methacrylate are omitted. After cooling, the pH of the dispersion is adjusted to 8 to 8.5 using about 20 ml of 17% strength by weight aqueous $NH_3$. The finely divided anionic dispersion has a solids content of 34% by weight and a MFT of 11° C.

Application Tests

The biocidal activity of the dispersions according to the invention can be assessed by painting testpieces composed of wood (board test) or composed of filter paper (algae filter test) with, in each case, one of the dispersions, according to the invention, of Examples 1 to 5 and, for comparison, with dispersions of Comparison Examples 1 and 2, which are not according to the invention and contain comparable amounts of solids and placing them either on a microbially infected agar-agar nutrient medium or in a green algae culture and observing the biocidal activity against fungi and algae. In detail, the procedure used can be as described below.

Board Test

The board test is used to test whether a wood coating offers adequate protection against fungal growth. To this end, pine sap wood boards having dimensions of 50×25×5 mm (fiber direction 50 mm) are either coated on one side or treated in accordance with another given form of application for wood protection agents (for example brief dipping) with the biocidal dispersion or solution to be tested. After drying in air for four weeks at RT, the coated or dip-treated board testpieces are placed, after sterilization by UV light, with a treated testpiece surface on infected and pre-incubated nutrient media which had been inoculated with molds (*Aspergillus niger*) or blue fungi (*Sclerophoma pityophila* and Aureobasidium pullulans) or soft rot fungi (Chaetomium globosom).

The board testpieces inoculated with fungi via the preincubated nutrient media are stored in an incubator at 29° C. and 70% relative atmospheric humidity for 4 weeks and the fungal growth on the testpiece is then assessed in accordance with the following rating scale 0 to 4.

| | |
|---|---|
| OH > 3 = | no growth on the wood and inhibitory zone more than 3 mm wide on the agar nutrient medium adjacent to the testpiece |
| OH < 3 = | no growth on the wood and inhibitory zone less than 3 mm wide on the agar nutrient medium next to the testpiece |
| 0 = | no growth on the wood, no inhibitory zone next to the testpiece on the agar nutrient medium |
| 1 = | slight growth on the wood, covering less than 10% |
| 2 = | growth on the wood, covering less than 30% |
| 3 = | distinct growth on the wood, covering 30 to 60%, wood attacked |
| 4 = | severe growth on the wood, covering more than 60%, entire wood attacked. |

In order to assess the waterproof properties or the leachability of the biocidal active compound, in a further test the primed or painted or dip-treated and dried testpieces described above are watered, in each case for 48 hours, 96 hours and 1 month, in running water, then dried again, rendered germ-free by means of UV light and placed in Petri dishes on the prepared and in each case specifically infected agar-agar nutrient media. Incubation and subsequent assessment of the samples in the Petri dishes are carried out in a manner analogous to that described above for the unwatered samples.

Algae Filter Test

The protection against attack by algae is tested. To this end, painted coatings are infected with algae and placed under standardized growth conditions. In the case of a good algicidal action, the algae must not grow on the paint coating.

In order to test the leachability of the algicide, the paint coatings are watered for two days, four days and 1 month prior to infection with algae. The effectiveness should not be substantially reduced as a result.

Test Procedure

Round paper filters having a diameter of 5.5 cm are painted on one or both sides with the dispersion to be tested and dried at room temperature for 2 to 3 days. The weight of the dry film is determined by weighing before and after painting. After drying, individual filters are placed in running water, in each case for 48 or 96 hours or 1 month, and then dried again.

Prior to infection with algae, the dry filters are sterilized on both sides under UV light and placed individually in sterile glass Petri dishes of 9 cm $\phi$. The infection with 10 ml of green algae culture (strain used: Chlorella pyrenoidosa), which has been cultured in a Knop nutrient solution and is 8 to 21 days old, then follows.

The test is carried out at 16° to 20° C. in a chamber with diffuse light. In order to promote more rapid growth of the green algae, light is provided at night. After 14 days, the paint coatings are assessed in accordance with the following rating scale O to III:

| | |
|---|---|
| 0 = | no growth on the paint coating |
| I = | slight growth on the paint coating |
| II = | distinct growth on the paint coating |
| III = | severe growth on the paint coating. |

The results are summarized in Table 2. They show the outstanding inhibitory action of biocidal paint coatings, according to the invention, from Examples 1 to 5, both in the fungus inhibition test and in the algae inhibition test, and in each case also after prior watering of the paint coating for up to 1 month, compared with paint coatings of the BCM-free plastic dispersions of Comparison Examples 1 and 2, which are not according to the invention, and the commercially available biocidal wood protection scumble Sadolin classic from Sadolin GmbH. In this context it is particularly noteworthy that the samples preserved according to the invention show virtually no loss of their fungus-inhibiting action as a result of watering, the amphoteric dispersion of Example 4 and the cationic dispersion of Example 5 are, in addition, characterized by an exceptionally strong algicidal action and the samples according to the invention, compared with samples which have been painted with conventional dispersions according to Comparison Examples 1 and 2 or with Sadolin classic, also display unexpectedly good inhibitory properties overall per se, as already mentioned.

TABLE 2

Test to determine the biological inhibitory action of paint coatings composed of biocidal plastic dispersions on wood testpieces and filter paper [W = wood testpiece; F = filter paper testpiece; w.w. = test without prior watering of the testpiece; h-w = prior testpiece watering period in hours, or m-w in months; fungus test period = 4 weeks, rating scale 0 (no attack by fungi) to 4 (severe attack by fungi).
Algae test period = 14 days, rating scale 0 (no growth of algae) to III (severe growth of algae)]
Biological test organisms and test result rating figures

| Testpiece paint coating composed of plastic dispersion from | Blue fungi | | | | Molds | | | |
|---|---|---|---|---|---|---|---|---|
| | w.w. | 48 h-w. | 96 h-w. | 1 m-w. | w.w. | 48 h-w. | 96 h-w. | 1 m-w. |
| Example 1 (W) | CH > 3 | CH > 3 | CH > 3 | 0 | 0 | 0 | 0 | 0 |
| Example 1 (F) | | | | | | | | |
| Example 2 (W) | 0 | 0 | 0 | 0 | 0 | 1 | 1 | 2 |
| Example 2 (F) | | | | | | | | |
| Example 3 (W) | CH > 3 | CH > 3 | CH > 3 | CH > 3 | CH > 3 | 0 | CH > 3 | 0 |
| Example 3 (F) | | | | | | | | |
| Example 4 (W) | 0 | 0 | 0 | 1 | 0 | 0 | 2 | 1 |
| Example 4 (F) | | | | | | | | |
| Example 5 (W) | CH > 3 | CH > 3 | CH > 3 | CH > 3 | CH > 3 | CH > 3 | CH > 3 | CH > 3 |
| Example 5 (F) | | | | | | | | |
| Comp. Ex. 1 (W) | 4 | 4 | 4 | 4 | 4 | 4 | 4 | 4 |
| Comp. Ex. 1 (F) | | | | | | | | |

TABLE 2-continued

| Comp. Ex. 2 (W) | 4 | 4 | 4 | 4 | 4 | 4 | 4 | 4 |
|---|---|---|---|---|---|---|---|---|
| Comp. Ex. 2 (F) | | | | | | | | |
| Commercially available wood protection scumble (Sadolin classic) | 0 | 0 | 1 | 3 | 4 | 4 | 4 | 4 |

| Testpiece paint coating composed of plastic dispersion from | Soft rot molds | | | | Algae | | | |
|---|---|---|---|---|---|---|---|---|
| | w.w. | 48 h-w. | 96 h-w. | 1 m-w. | w.w. | 48 h-w. | 96 h-w. | w.w. |
| Example 1 (W) | CH > 3 | CH > 3 | CH > 3 | CH > 3 | | | | |
| Example 1 (F) | | | | | 0 | 0 | I | II |
| Example 2 (W) | 0 | 0 | 1 | 2 | | | | |
| Example 2 (F) | | | | | 0 | I | II | III |
| Example 3 (W) | 0 | 0 | 0 | 0 | | | | |
| Example 3 (F) | | | | | 0 | 0 | II | II |
| Example 4 (W) | 0 | 0 | 1 | 1 | | | | |
| Example 4 (F) | | | | | 0 | 0 | 0 | 0 |
| Example 5 (W) | CH > 3 | 0 | CH > 3 | 0 | | | | |
| Example 5 (F) | | | | | 0 | 0 | 0 | 0 |
| Comp. Ex. 1 (W) | 4 | 4 | 4 | 4 | | | | |
| Comp. Ex. 1 (F) | | | | | I | II | III | III |
| Comp. Ex. 2 (W) | 4 | 4 | 4 | 4 | | | | |
| Comp. Ex. 2 (F) | | | | | I | II | II | III |
| Commercially available wood protection scumble (Sadolin classic) | 1 | 3 | 4 | 4 | | | | |

We claim:

1. A biocidal polymer or copolymer based on free radical-polymerized or copolymerized ethylenically unsaturated monomers, wherein the polymer or copolymer contains monomer units composed of BCM salts of the formula I

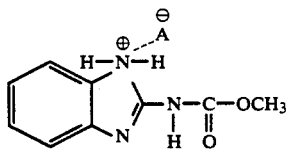
(I)

in which $A^{\ominus}$ is an anionic ethylenically unsaturated carboxylic acid or sulfonic acid or phosphonic acid radical, and said monomer units are polymerized in the biocidal macromolecule via the ethylenic double bond of the radical $A^{\ominus}$, or a solution or aqueous dispersion of said polymer or copolymer.

2. A biocidal copolymer as claimed in claim 1, which contains 0.001 to 5 % by weight, with respect to the biocidal copolymer, of monomer units composed of BCM salts of the formula I.

3. A biocidal polymer or copolymer as claimed in claim 1, which contains monomer units composed of BCM salts of the formula I, in which, in formula I, the anionic radical $A^{\ominus}$ is an acrylate, methacrylate, fumarate, maleate, crotonate, itaconate, styrenesulfonate, acrylamidomethylpropanesulfonate, acrylamidoglycolicacid methyl ether, vinylsulfonate, vinylphosphonate or acrylamidomethylphosphonate radical.

4. A biocidal aqueous copolymer dispersion as claimed in claim 1, wherein the dispersion contains a dispersion copolymer in which the macromolecules contain monomer units, calculated in a % by weight with respect to the copolymer, selected from the monomer groups consisting of a) 80 to 99.9% by weight, of ethylenically unsaturated hydrophobic monomers selected from the group consisting of vinyl esters, methacrylic esters, acrylic esters and vinyl-aromatic compounds, b) 0.001 to 5% by weight, of BCM salts of the formula I in which A has the meaning indicated in claim 1, c) 0 to 10% by weight, of ethylenically unsaturated cationic water-soluble monomers, which contain as cationic groups, quaternized alkylammonium, alkyl-sulfonium or alkylphosphonium groups, the alkyls in each case have 1 to 24 carbon atoms, optionally replaced by ($C_3$-$C_7$)-cycloalkyl, $C_7$-$C_{12}$)-aralkyl or ($C_1$-$C_{18}$ )-alkyl radicals or —$CH_2CONH_2$, and d) 0 to 19% by weight, of ethylenically unsaturated hydrophilic monomers containing one or more functional groups selected from the group consisting of —OH, —COOH, —$SO_3$H, —PO(OH) and —CONR$^1$R$^2$, R$^1$ and R$^2$ are individually H or —$CH_2$OR, where R=H or ($C_1$-$C_8$)-alkyl, and the dispersions also contain 0.2 to 20% by weight, of surface-active compounds selected from the group consisting of anionic, nonionic, cationic or amphoteric emulsifiers and can also contain between 0 and 5% by weight, of protective colloids, in each case with respect to the total amount of monomer.

5. A biocidal polymer or copolymer as claimed in claim 1, which is in the form of an aqueous anionic or cationic or amphoteric dispersion, the solids content of which is 5 to 70% by weight, with respect to the dispersion, and the minimum film-forming temperature (MFT) of which is in the range from 0° to 80° C.

* * * * *